(12) United States Patent
Dahne et al.

(10) Patent No.: US 10,959,919 B2
(45) Date of Patent: *Mar. 30, 2021

(54) HAIR TREATMENT METHOD AND KIT THEREOF

(71) Applicant: Coty Inc., New York, NY (US)

(72) Inventors: Lars Siegfried Dahne, Berlin (DE); Mathias Kurt Herrlein, Kronberg (DE); Ingo Weber, Gruenstadt (DE); Markus Speckbacher, Schwalbach (DE); Mandy Hecht, Falkensee (DE); Simon Paul Godfrey, Oberursel (DE)

(73) Assignee: Wella Operations US, LLC, Calabasas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/488,015

(22) PCT Filed: Oct. 5, 2018

(86) PCT No.: PCT/US2018/054717
§ 371 (c)(1),
(2) Date: Aug. 22, 2019

(87) PCT Pub. No.: WO2019/071204
PCT Pub. Date: Apr. 11, 2019

(65) Prior Publication Data
US 2019/0380922 A1    Dec. 19, 2019

(30) Foreign Application Priority Data

Oct. 6, 2017   (EP) .................................. 17195273

(51) Int. Cl.
| | |
|---|---|
| *A61K 8/02* | (2006.01) |
| *A61K 8/19* | (2006.01) |
| *A61K 8/23* | (2006.01) |
| *A61K 8/25* | (2006.01) |
| *A61K 8/26* | (2006.01) |
| *A61K 8/27* | (2006.01) |
| *A61K 8/29* | (2006.01) |
| *A61K 8/86* | (2006.01) |
| *A61Q 5/10* | (2006.01) |

(52) U.S. Cl.
CPC .............. *A61K 8/0241* (2013.01); *A61K 8/19* (2013.01); *A61K 8/23* (2013.01); *A61K 8/25* (2013.01); *A61K 8/26* (2013.01); *A61K 8/27* (2013.01); *A61K 8/29* (2013.01); *A61K 8/86* (2013.01); *A61Q 5/10* (2013.01)

(58) Field of Classification Search
CPC ... A61K 8/02; A61K 8/19; A61K 8/23; A61K 8/25; A61K 8/26; A61K 8/27; A61K 8/29; A61K 8/86; A61Q 5/10
See application file for complete search history.

(56) References Cited

U.S. PATENT DOCUMENTS

| | | | |
|---|---|---|---|
| 2008/0108740 | A1 | 5/2008 | Evers |
| 2010/0088036 | A1 | 4/2010 | Goddard-Clark et al. |
| 2011/0061179 | A1* | 3/2011 | Cremer ................. C09B 69/101 8/407 |

FOREIGN PATENT DOCUMENTS

| | | | |
|---|---|---|---|
| CN | 111432887 A | | 7/2020 |
| DE | 19913625 A1 | | 9/2000 |
| EP | 0132960 A2 | | 2/1985 |
| WO | WO 2009073759 | * | 6/2009 |
| WO | WO 2017/189585 | * | 11/2017 |
| WO | WO-2019071204 A | | 4/2019 |

OTHER PUBLICATIONS

"European Application Serial No. 17195273.2, Extended European Search Report dated Jan. 11, 2018", 8 pgs.
"International Application Serial No. PCT/US2018/054717, International Search Report dated Dec. 20, 2018", 5 pgs.
"International Application Serial No. PCT/US2018/054717, Written Opinion dated Dec. 20, 2018", 7 pgs.
Barber, David, et al., "A Logical Stepwise Approach to Laser Diffraction Particle Size Distribution Analysis Methods Development and Validation", Pharmaceutical Development and Technology, 3(2), (1998), 153-161.
"International Application Serial No. PCT/US2018/054717, International Preliminary Report on Patentability dated Apr. 16, 2020", 9 pgs.

* cited by examiner

*Primary Examiner* — Shirley V Gembeh
(74) *Attorney, Agent, or Firm* — Victoria Friedman; Dennemeyer & Associates LLC

(57) ABSTRACT

A method for treating hair comprising applying at least one pigment onto hair for providing the basis for colouring hair in a more reproducible and reliable manner independently from a user's initial hair colour.

19 Claims, No Drawings

HAIR TREATMENT METHOD AND KIT THEREOF

CLAIM OF PRIORITY

This patent application is a U.S. National Stage Filing under 35 U.S.C. 371 from international Application No. PCT/US2018/054717, filed on Oct. 5. 2018, and published as WO 2019/071204 on Apr. 11, 2019, which application claims the benefit of priority to European Application Serial No. 17195273.2, filed Oct. 6, 2017, which are incorporated by reference herein in their entirety.

FIELD OF THE INVENTION

The invention is directed to a method for treating hair comprising applying at least one pigment onto hair for providing the basis for colouring hair in a more reproducible and reliable manner independently from a user's initial hair colour.

BACKGROUND OF THE INVENTION

Different methods for changing the colour of hair are known in the art. These methods involve the use of hair colouring compositions which allow either permanent or temporary change of hair colour.

Hair colouring compositions which are used to permanently change the colour of hair, also called oxidative hair colouring compositions, typically comprise oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of colour. This reaction typically takes place at approximately pH 10 to 11 in the presence of an alkalizing agent and an oxidizing agent. Typically an oxidizing composition (also called developer and/or oxidizing component) comprising the oxidizing agent and a dye composition (also called tint or dye component) comprising the alkalizing agent and if present the hair dye precursors are mixed shortly before use. The consumer repeats this process regularly in order to maintain the desired hair colour, shade and intensity of colour and to ensure continual, even coverage of the hair including coverage of new hair growth. The problem with standard oxidative hair colouring methods is that the conditions under which the reaction is taking place, i.e. the high pH value as well as the presence of an oxidizing agent may cause damage to the structure of the hair and may be irritating for the scalp of the user, especially when such a process is repeated regularly and the compositions which are usually used have an undesirable odour. An even more severe problem is that obtaining the desired target colour is fairly difficult since standard oxidative hair colouring compositions are highly reactive compositions and since it is therefore not easy to completely control and predict the reaction on hair.

As an alternative to the use of the above described oxidative hair colouring compositions, methods for temporarily changing the colour of hair have also been developed. For instance, these methods usually involve the application of hair colouring compositions comprising direct dyes. The hair colouration obtained by direct dyes is typically characterized by a weaker washfastness than when the hair is coloured with standard oxidative hair colouring compositions, i.e. the colouration is typically fading after regular washing of the hair with standard shampoo compositions. Direct dye compositions are usually less aggressive for the hair since they are non-reactive compositions. However, since direct dyes are low molecular weight molecules, they may have the tendency to also colour the scalp of the user. Moreover, achieving a predetermined target colour in a reproducible and reliable manner is fairly difficult since the final colour obtained by using direct dyes very much depends on the initial colour and condition of the user's hair. For instance, two users with different initial hair colours will obtain different hair colours after using one and the same direct dye. Moreover, even for one and the same user having an initial hair colour, the final hair colour obtained by colouration may very much depend on the initial condition of the hair during colouration. For instance, it may be of importance whether or not the hair have been washed before, when the hair have been washed, the type of shampoo used etc. As such, one and the same user applying one and the same dye on different days can hardly rely on obtaining one and the same final colour.

Apart from the use of direct dyes, other methods for temporarily changing the colour of hair have also been developed. These methods involve the application of hair colouring compositions comprising polymeric dyes. Similar to direct dyes, a hair colouration obtained by polymeric dyes is also typically characterized by a weaker washfastness than when the hair is coloured with standard oxidative hair colouring compositions. Moreover, the final colour obtained by applying polymeric dyes is also hardly predictable for similar reasons as described for direct dyes.

With the foregoing in view, there is a need for a method for achieving a predetermined target colour in a more reproducible and reliable manner independently from the user's initial hair colour and hair condition. This method should preferably involve the use of compositions which are less aggressive for the hair and for the scalp. Finally, this method should also preferably involve the use of low odour compositions.

The inventors have surprisingly found out that at least some of these needs may be met by the method for treating hair according to the present invention, wherein a composition A comprising at least one pigment is applied onto the hair to impart the hair with an intermediate colour which is different to the initial colour, and wherein upon subsequent colouration, a predetermined target colour can be achieved in a more reliable and reproducible manner.

SUMMARY OF THE INVENTION

The present invention relates to a method for treating hair comprising:
A) applying a composition A comprising at least one pigment to a first portion of the hair having a first initial colour to impart the first portion of the hair with a second colour different to the first initial colour,
  wherein the at least one pigment has a $D_{50}$ particle diameter of 20 nm to 1 μm, and
  wherein the difference between the L* value of the second colour and the L* value of the first initial colour $L*_{second\ colour} - L*_{initial\ first\ colour}$ is ≥1 according to the CIE L* a* b* system.

The present invention further relates to a method for treating hair comprising:
A) applying a composition A comprising at least one pigment to a first portion of the hair having a first initial colour to impart the first portion of the hair with a second colour different to the first initial colour, wherein the overall colour change, represented by $\Delta E$ where $\Delta E=[(\Delta L^*)^2+(\Delta a^*)^2+(\Delta b^*)^2]^{1/2}$, from the first initial colour to the second colour is $\geq 5$, and wherein the L* value of the second colour $L^*_{second\ colour}$ is higher than the L* value of the first initial colour $L^*_{initial\ first\ colour}$, according to the CIE L* a* b* system.

The present invention further relates to a method for treating hair comprising:

A) applying a composition A comprising at least one pigment to a first portion of the hair having a first initial colour to impart the first portion of the hair with a second colour different to the first initial colour, the at least one pigment having a $D_{50}$ particle diameter of 20 nm to 1 µm, the at least one pigment further having a L* value $L^*_{Pigment}$ of $\geq 60$ according to the CIE L* a* b* system, wherein the second colour has a L* value $L^*_{second\ colour}$ of $\geq 22$ according to the CIE L* a* b* system.

The present invention further relates to a method for treating hair comprising:

A) applying a composition A comprising at least one pigment to a first portion of the hair having a first initial colour to impart the first portion of the hair with a second colour different to the first initial colour, the at least one pigment having a $D_{50}$ particle diameter of 20 nm to 1 µm, the at least one pigment further having a surface zeta potential of $\geq \pm 15$ mV, wherein the second colour has a L* value $L^*_{second\ colour}$ of $\geq 22$ according to the CIE L* a* b* system.

The present invention further relates to a method for treating hair comprising carrying out the following sequence of steps:

applying one or more polymeric sublayer(s) to the hair, and applying a composition A comprising at least one pigment to the hair having a first (initial) colour to impart the hair with a second colour different to the first (initial) colour, wherein the at least one pigment has a $D_{50}$ particle diameter of 20 nm to 1 µm.

The present invention further relates to a method for treating hair comprising:

applying a composition A comprising at least one pigment to a first portion of the hair having a first initial colour to impart the first portion of the hair with a second colour different to the first initial colour, the at least one pigment having a $D_{50}$ particle diameter of 20 nm to 1 µm, the at least one pigment having a core-shell structure, wherein the core comprises an inorganic and/or organic material, and wherein the shell comprises at least one cationic polymeric layer.

The present invention further relates to a method for treating hair comprising carrying out the following sequence of steps:

determining a target colour, wherein the target colour differs from a first initial colour of the hair.

applying a composition A comprising at least one pigment to a first portion of the hair to impart the first portion of the hair with a second colour different to the first initial colour, and applying one or more hair colouring composition(s) to a second portion of the hair to impart the second portion of the hair with a third colour different to the second colour, wherein the first and second portions have at least one first common area.

The present invention further relates to a hair treatment composition comprising a core-shell pigment, wherein the core of the pigment comprises an inorganic and/or organic material, and wherein the shell of the pigment comprises at least one cationic polymer, the at least one core-shell pigment having a $D_{50}$ particle diameter of 20 nm to 1 µm.

The present invention further relates to a kit for treating hair comprising:

a first component comprising a composition A comprising a pigment as defined herein, and optionally a second component comprising a composition B1 comprising a cationic polymer as defined herein.

The present invention further relates to the use of a component comprising the composition A as defined herein for changing a hair colour from a first initial colour via a second intermediate colour to a third final colour, wherein the third final colour differs from a predetermined target colour in at most 5% of at least one of:

a* value, b* value, and

L* value, according to the CIE L* a* b* system.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All ratios or percentages are weight ratios or weight percentages unless specifically stated otherwise.

By "cationic polymer" it is meant any polymer comprising an overall charge at full protonation which is positive.

By "cationic coloured polymer" it is meant any cationic polymer comprising at least one chromophore and/or at least one fluorophore either in the skeleton or as pendent group.

By "cationic uncoloured polymer" it is meant any cationic polymer which does not comprise any chromophore or fluorophore either in the skeleton or as pendent group.

By "anionic polymer" it is meant any polymer comprising an overall charge at full deprotonation which is negative.

By "anionic coloured polymer" it is meant any anionic polymer comprising at least one chromophore and/or at least one fluorophore either in the skeleton or as pendent group.

By "anionic uncoloured polymer" it is meant any anionic polymer which does not comprise any chromophore or fluorophore either in the skeleton or as pendent group.

By "full protonation" it is meant the state at which the different protonable groups of a polymer are all fully protonated.

By "full deprotonation" it is meant the state at which the different deprotonable groups of a polymer are all fully deprotonated.

By "weak cationic polymer" it is meant a cationic polymer whose charge is dependent on the pH when solubilized in water.

Method for Treating Hair

The present invention is generally concerned with a method for treating hair comprising applying one or more cationic polymer(s) as defined herein and/or one or more pigment(s) as defined herein to a portion of the hair. In principle, the one and more cationic polymer(s) can be applied together with the one and more pigment(s), or alternatively, they may be applied in separate steps in any possible sequence. For instance, the one or more cationic polymer(s) can be applied to the hair in a first step followed by applying the one or more pigment(s) in a subsequent step, or vice versa.

More specifically, the present invention relates to a method for treating hair comprising:

A) applying a composition A comprising at least one pigment to a first portion of the hair having a first initial colour to impart the first portion of the hair with a second colour different to the first initial colour.

Step A)

In step A) of the method according to the present invention, a composition A comprising one or more pigment(s) is applied to a first portion of the hair having a first initial colour to impart the first portion of the hair with a second (intermediate) colour different to the first initial colour.

By "first initial colour" of the hair it is meant the starting colour of the user's hair immediately prior to step A). By carrying out step A), the colour of the user's hair is changed in the first hair portion from the first initial colour to a second (intermediate) colour. By "second (intermediate) colour" it is meant a transitional colour the user's hair is imparted with before the hair is preferably coloured to a third final colour in a subsequent step. The second (intermediate) colour is different to the first initial colour. The overall color change, represented by $\Delta E$ where $\Delta E=[(\Delta L^*)^2+(\Delta a^*)^2+(\Delta b^*)^2]^{1/2}$, from the first initial colour to the second (intermediate) colour may be $\geq 5$, typically $\geq 8$, more typically $\geq 12$, more typically $\geq 15$, more typically $\geq 18$, according to the CIE L* a* b* system. Typically, the L*-value of the second colour ($L^*_{second\ colour}$) may be higher than the L*-value of the first initial colour ($L^*_{first\ initial\ colour}$). The $\Delta L^*$ between the first initial colour and the second (intermediate) colour is at least 1, typically at least 5, more typically at least 10, more typically at least 15, even more typically at least 20, according to the CIE L* a* b* system. In other words, the difference between the L* value of the second colour and the L* value of the first initial colour $L^*_{second\ colour}-L^*_{initial\ first\ colour}$ is $\geq 1$, typically $\geq 5$, more typically $\geq 10$, more typically $\geq 15$, even more typically $\geq 15$, according to the CIE L* a* b* system. The second colour may have a L* value of $\geq 22$, typically $\geq 25$, more typically $\geq 30$, more typically $\geq 35$, more typically $\geq 40$, according to the CIE L* a* b* system. L*, a*, and/or b* values are preferably measured by using a Minolta spectrometer according to the manufacturers' instructions for use. Colour measurements are conducted, for example, according to ISO 7724.

Composition A

The composition A may be applied to a first portion of the hair, and may preferably be applied all over the hair.

The composition A may be applied in one go or step-by-step to the hair. The composition A may be applied step-by-step, for example in case the hair is damaged. Applying the composition A step-by-step, may help to ensure that the hair is saturated with the composition A and may therefore provide a better coverage of the hair with the composition A.

The composition A may comprise a total amount of pigments ranging from 1% to 50%, particularly from 5% to 40%, more particularly from 10% to 30%, or from 10% to 20% particularly from 12% to 18%, more particularly from 14% to 16%, or from 20% to 30% particularly from 22% to 28%, more particularly from 24% to 26%, or from 30% to 50%, particularly from 35% to 45%, more particularly from 38% to 42% pigment by total weight of the composition.

Pigment(s)

The pigment(s) may be present in the composition A in undissolved form. The pigments may have a $D_{50}$ particle diameter of from 20 nm to 1 micron, typically 60 nm to 900 nm, more typically 100 nm to 600 nm. Particle diameter is represented by $D_{50}$, which is the median diameter by volume. $D_{50}$ is measured with a Malvern Mastersizer 2000, which is a laser diffraction particle sizer and it is measured according to ISO 13320:2009(en) with Hydro 2000G or Hydro 2000S where the dispersant is water or ethanol. Detection range is from 0.01 micron to 2000 micron. $D_{50}$ is expressed as $x_{50}$ in ISO 13320:2009(en). Laser diffraction measures particle size distributions by measuring the angular variation in intensity of light scattered as a laser beam passes through a dispersed particulate sample analyser and the particle size is reported as a volume equivalent sphere diameter. A discussion of calculating $D_{50}$ is provided in Barber et al, Pharmaceutical Development and Technology, 3(2), 153-161 (1998), which is incorporated herein by reference. Pigment(s) having a D50 particle diameter of <20 nm do not provide a light scattering effect anymore. Pigment(s) having a D50 particle diameter of >1 μm do not sufficiently adhere onto hair fibres.

The pigment(s) may be colorants which are virtually insoluble in the composition. As such, the pigment(s) may be coloured pigments which impart colour effects to the hair (keratin fibres), or they may be lustre effect pigment(s) which impart desirable and aesthetically pleasing lustre effects to the hair (keratin fibres).

The pigment(s) may be inorganic or organic. Inorganic-organic mixed pigment(s) are also possible. Preference is given to inorganic pigment(s). The advantage of inorganic pigment(s) is their excellent resistance to light, weather and temperature. The inorganic pigment(s) may be of natural origin, and are, for example, derived from material selected from the group consisting of chalk, ochre, umber, green earth, burnt sienna, and graphite. The pigment(s) may preferably be white pigments, such as, for example, titanium dioxide or zinc oxide. The pigment(s) may also be coloured pigments, such as, for example, ultramarine or iron oxide red, lustre pigments, metal effect pigments, pearlescent pigments, and fluorescent or phosphorescent pigments. The pigment(s) may be selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze pigments). The pigment(s) may be selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminium sulfosilicates, CI 77007, Pigment Blue 29), chromium oxide hydrate (CI 77289), Prussian blue (ferric ferrocyanide, CI 77510), carmine (cochineal), zinc sulfide, barium sulfate, zinc oxide, siliconised titanium dioxide, siliconised zinc sulfide, siliconised zinc oxide, and mixtures thereof.

The pigment(s) may be pearlescent and coloured pigment(s), and may preferably be based on mica which are coated with a metal oxide or a metal oxychloride, such as titanium dioxide or bismuth oxychloride, and optionally further colour-imparting substances, such as iron oxides, Prussian blue, ultramarine, and carmine. The colour exhibited by a pigment can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for colour travel pigments that display colour shifting effects depending on the viewing angle and are based on either natural mica, $SiO_2$ or calcium aluminium borosilicate flakes, coated with varying layers of $TiO_2$. Pigment(s) from the line KTZ® from Kobo Products, Inc., 3474 So. Clinton Ave., So. Plainfield, USA, are also useful herein, in particular the Surface Treated KTZ® Pearlescent Pigments from Kobo. Particularly useful are KTZ® FINE WHITE (mica and $TiO_2$) having a $D_{50}$ particle diameter of 5 to 25 micron and also KTZ® CELESTIAL LUSTER (mica and $TiO_2$, 10 to 60 micron) as well as KTZ® CLASSIC WHITE (mica and $TiO_2$, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection colour and is composed of platelets of synthetic fluorphlogopite and coated with titanium dioxide and iron oxides. Also useful is Duocrome® RV 524C from BASF, which provides a two colour look via a lustrous red powder with a violet reflection powder due to its composition of mica, titanium dioxide and carmine. The coloured pigment(s) may be lightly bright coloured pigment(s), and may preferably be white colour variations.

The pigment(s) may be organic pigments. The organic pigment(s) may be selected from the group consisting of natural pigments sepia, gamboge, bone charcoal, Cassel brown, indigo, chlorophyll and other plant pigments. The synthetic organic pigments may be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof. A particularly preferred pigment is 7-Bis(1,3-dichloropropan-2-yl)benzo[lmn][3,8]phenanthrolin-1,3,6,8(2H,7H)-tetraon.

The pigment(s) may be selected from the group consisting of iron oxide, titanium dioxide, mica, borosilicate, and combinations thereof. The pigment(s) may comprise an iron oxide ($Fe_2O_3$) pigment. The pigment(s) may comprise a combination of mica and titanium dioxide.

The pigment(s) may have a surface zeta potential of $\geq \pm 15$ mV, typically $\geq \pm 20$ mV, more typically $\geq \pm 25$ mV. The surface zeta potential can be measured with a zetasizer, for example, a Zetasizer 3000 HS. Surface zeta potential measurements are conducted, for example, according to ISO 13099.

The pigment(s) may have a L* value of $\geq 60$, typically $\geq 80$, more typically $\geq 90$ according to the CIE L* a* b* system. The colorimetric parameters in the CIE L* a* b* system are measured with a Minolta CM-508i spectrophotometer (illuminant is D65 daylight with 10° observer) in which L* represents the lightness of the colour, a* indicates the green/red colour axis and b* the blue/yellow colour axis.

The pigment(s) may exist in the form of spheres, flakes, whiskers, or shapes approximating these forms. The pigment(s) may have a cross-sectional geometry that may be circular, ellipsoidal, triangular, rectangular, polygonal, or a combination comprising at least two of the foregoing geometries. In a particular aspect, the pigment(s) may have a shape approximating that of a sphere. In other words, the pigment(s) may have a "spherical-type" shape. A pigment(s) having a "spherical-type" shape is understood as a particle having an aspect ratio, defined as a function of the smallest diameter $d_{min}$ and the largest diameter $d_{max}$ orthogonal to it: $AR=d_{min/dmax}$ which is preferably from 0.3 to 1, more preferably from 0.4 to 1, most preferably from 0.5 to 1. More preferably, the expression "spherical-type" means that the pigment(s) have a shape approximating that of a sphere. In other words, the pigment(s) may be nearly orbicular in shape and may have a cross-sectional geometry that is essentially circular. Although not excluded, this does not necessarily mean that the pigment(s) have the shape of a perfect sphere or ball. More likely, the shape of the pigment(s) may exhibit a certain deviation from a sphere as long as the skilled person considers the shape as being similar to a sphere or as an approximation of a sphere.

The pigment(s) may have a "core-shell structure" (core-shell morphology). In the case that the pigment(s) have a "core-shell structure", the "core" corresponds to the "naked" pigment which features the same properties as defined hereinbefore with reference to the "pigment(s)". The "shell" corresponds to a coating layer surrounding the "core". The pigments having a core-shell structure may have a $D_{50}$ particle diameter of from 20 nm to 1 micron, typically 60 nm to 900 nm, more typically 100 nm to 600 nm. D50, the median diameter by volume, is defined as hereinbefore. As such, the present invention also relates to a hair treatment composition comprising a core-shell pigment, wherein the core of the pigment comprises an inorganic and/or organic material, and wherein the shell of the pigment comprises at least one cationic polymer, the at least one core-shell pigment having a $D_{50}$ particle diameter of 20 nm to 1 µm.

The shell surrounding the core may comprise one or more polymeric shell layers. Typically, the shell may comprise a cationic polymeric shell layer.

The cationic polymeric shell layer is typically made of one or more cationic polymer(s). Optionally, an anionic polymeric shell layer may be positioned (arranged) on top of the cationic polymeric shell layer. An anionic polymeric shell layer is typically made of one or more anionic polymer(s). Together, the cationic polymeric shell layer and the anionic polymeric shell layer form a first polymeric shell double layer. Optionally, additional shell layer(s) may be positioned (arranged) on top of the first polymeric shell double layer. For instance, only one additional cationic polymeric shell layer may be positioned (arranged) on top of the anionic shell layer of the first polymeric shell double layer. Alternatively, one additional cationic polymeric shell layer may be positioned (arranged) on top of the anionic shell layer of the first polymeric shell double layer followed by one additional anionic polymeric shell layer to form a second polymeric shell double layer. As such, the shell surrounding the core may comprise more than one polymeric shell double layers, and typically, the shell may comprise one, two, three or four polymeric shell double layers.

If desired, a final cationic polymeric shell layer may be positioned (arranged) on top of the uppermost polymeric shell double layer. This may enhance the adhesion between the pigment(s) having a core-shell structure and hair fibers for the following reasons. Hair is naturally negatively charged. Therefore, the final shell layer of the coated hair which is positively charged can easily attach to the surface of the hair.

The Cationic Polymeric Shell Layer(s)

The cationic polymeric shell layer(s) may be made of one or more cationic polymer(s).

The cationic polymer(s) may be coloured.

The cationic polymer(s) may preferably be uncoloured.

The cationic polymer(s) may comprise one or more amino functional group(s) per polymer chain, wherein the amino functional group(s) are selected from the group consisting of primary, secondary, tertiary, quaternary amino functional groups and mixtures thereof, preferably from the group consisting of secondary, tertiary, quaternary amino functional groups and mixtures thereof, more preferably from quaternary amino functional groups.

The cationic polymer(s) may be selected from the group consisting of polyethyleneimine, polyallylamine hydrochloride, polydiallyldimethylammonium chloride, polyvinylamine, copolymers thereof and mixtures thereof. The cationic polymer(s) may preferably be selected from the group consisting of polyethyleneimine, polydiallyldimethylammonium chloride, copolymers thereof and mixtures thereof.

The copolymers may be random or block copolymers.

The cationic polymer(s) may be linear or branched.

The cationic polymer(s) may be selected from the group consisting of:

a) Linear polyethyleneimine of the formula:

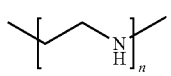

in which n is an integer representing the degree of polymerization, wherein n ranges from 50 to 20,000, alternatively from 100 to 3,500;

b) Branched polyethyleneimine consisting of primary, secondary and tertiary amine groups of the formula:

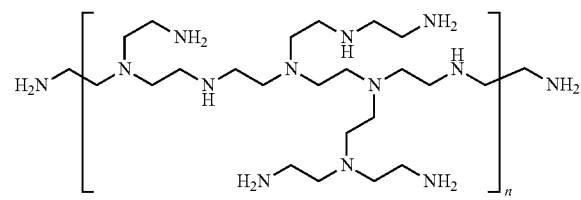

in which n is an integer representing the degree of polymerization, wherein n ranges from 5 to 4,000, alternatively from 50 to 500;

c) Polyallylamine hydrochloride of the formula:

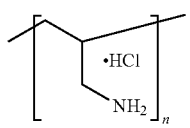

in which n is an integer representing the degree of polymerization, wherein n ranges from 50 to 20,000, alternatively from 150 to 2000;

d) Polydiallyldimethylammonium chloride of the formula:

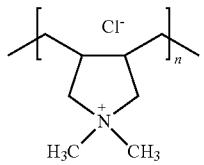

in which n is an integer representing the degree of polymerization, wherein n ranges from 10 to 20,000, alternatively from 150 to 4,000;

copolymers thereof and mixtures thereof.

The copolymers may be random or block copolymers.

The cationic polymer(s) may have a charge density at full protonation of at least 0.3, preferably at least 0.6, more preferably at least 0.8, even more preferably at least 1.0 positive charges per monomer unit.

The cationic polymer(s) may have a weight average molecular weight of more than 0.5 kD, preferably from 0.5 kD to 5000 kD, more preferably from 2 kD to 1000 kD, even more preferably from 10 kD to 200 kD, most preferably from 25 kD to 70 kD.

The Anionic Polymeric Shell Layer(s)

The anionic polymeric shell layer(s) may be made of one or more anionic polymer(s).

The anionic polymer(s) may be coloured.

The anionic polymer(s) may preferably be uncoloured.

The anionic polymer(s) may comprise one or more functional group(s) per polymer chain selected from the group consisting of phenyl group, alkyl groups comprising at least 8 carbon atoms and mixtures thereof.

The anionic polymer(s) may be selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof. The anionic polymer(s) may preferably be selected from the group consisting of polystyrene sulfonate salts, polystyrene sulfonate/polystyrene copolymer salts, copolymers thereof and mixtures thereof.

The copolymers may be random or block copolymers.

The anionic polymer(s) may be linear or branched.

The anionic polymers may be selected from the group consisting of:

a) Polystyrene sulfonate (PSS) sodium salt of the formula:

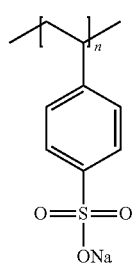

in which n is an integer representing the degree of polymerization, wherein n ranges from 50 to 20,000, alternatively from 150 to 2500;

b) Co-polymer of polystyrene sulfonate (PSS) sodium salt and poly(4-styrenesulfonic acid-co-maleic acid) of the formula:

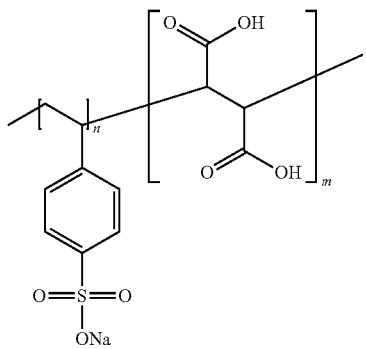

in which n and m are integers representing the degree of polymerization, wherein n+m ranges from 50 to 20,000, alternatively from 150 to 2500;

c) λ-Carrageenan;

d) Dextran sulfate sodium salt;

e) Polyacrylic acid (PAA) of the formula:

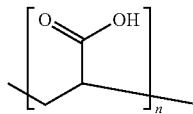

in which n is an integer representing the degree of polymerization, wherein n ranges from 50 to 20,000, alternatively from 150 to 1,000;

f) Alginic acid sodium salt;

g) Carboxymethylcellulose sodium salt of the formula:

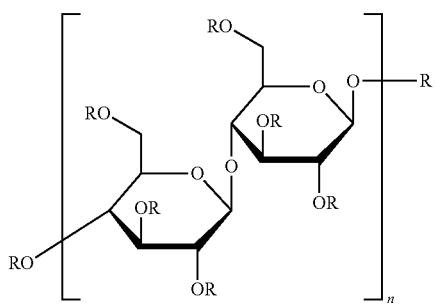

in which:

R is H or $(CH_2)_2COONa$ and n is an integer representing the degree of polymerization; copolymers thereof and mixtures thereof.

The copolymers may be random or block copolymers.

The anionic polymer(s) may have a charge density at full deprotonation of at least 0.3, alternatively at least 0.6, alternatively at least 0.8, alternatively at least 1.0 negative charges per monomer unit.

The anionic polymer(s) may have a weight average molecular weight of at least 1 kD, alternatively from 10 kD to 1000 kD, alternatively from 70 to 500 kD.

By carrying out step A), the composition A comprising the pigment(s) covers the surface of a user's hair to such an extent that the first initial hair colour (e.g. the natural hair colour) is substantially neutralized. Upon subsequent colouration, e.g., obtained through the application of polymeric dyes in step C) described below, the hair can be imparted with a third final colour which does not or only slightly differs from a target colour which has been predetermined by the user beforehand.

As such, the method according to the present invention is particularly advantageous since it is a feasible way for colouring the hair reproducible and reliable. Furthermore, the compositions which are used in the method according to the present invention are particularly advantageous since these compositions are less aggressive and exhibit low odor.

Film-Forming Resin(s)

The composition A may further comprise one or more film-forming resin(s). Alternatively, the composition A may be mixed with one or more film-forming resin(s) prior to applying it to hair in step A). By "film-forming resin" it is meant a hair-fixing polymer which forms a film on a surface. In the context of hair science, this surface is the surface of individual hair fibers or a plurality thereof. The hair-fixing polymer causes the hair fibers to be glued together to build welds, which are effectively crosslinks that provide the hold benefit. In concert, these welds form a 'hairnet' to provide hair hold and volume benefits to the consumer. When the net of welds is effectively formed, the hold and volume benefits can last all day and offer good resistance to environmental humidity. By building up a film on the hair surface, the pigment(s) contained in the composition A can be more effectively bonded to the hair surface, thereby preventing the pigment(s) from dropping off the fibers.

The film-forming resin(s) may be selected from aminosilicone polymer(s) and/or silicone resin(s).

Aminosilicone Polymer

The aminosilicone polymer typically comprises amino side chains, and wherein the aminosilicone polymer has a weight average molecular weight of from 10,000 Dalton to 60,000 Dalton. "side chain" in the context of a silicone refers to a group being not part of the silicone backbone nor only present on at least one terminus of the silicone backbone. "Terminal aminosilicone" as defined herein means silicone comprising one or more amino groups at one or both ends of the silicone backbone Aminosilicone polymers having amino side chains are sometimes referred to as silicone compounds comprising pendant amino groups. The aminosilicone polymer may be not a terminal aminosilicone. The composition may be substantially free of silicones having terminal amino groups.

The aminosilicone polymer is a film-forming aminosilicone polymer. The aminosilicone polymer may be a polydimethylsiloxane having graft amino groups.

The aminosilicone polymer may have a weight average molecular weight of from 15,000 Dalton to 50,000 Dalton, or from 20,000 Dalton to 40,000 Dalton.

The aminosilicone polymer may be a polydimethylsiloxane polymer having pendent (graft) amino groups. The aminosilicone polymer may conform to the formula:

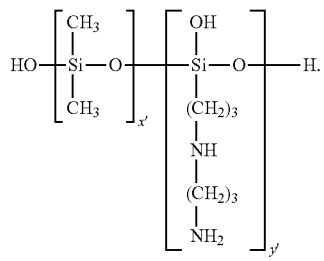

in which x' and y' are integers such that the weight average molecular weight is between 10,000 Dalton and 60,000 Dalton. The endcaps may be methoxy rather than hydroxyl as pictured in the above formula.

The aminosilicone polymer may be a polydimethylsiloxane polymer having a side chain with from 3 to 8 carbon atoms. The side chain may comprise carbon, hydrogen and nitrogen atoms. The side chain may consist of carbon, hydrogen and nitrogen atoms. The aminosilicone polymer may be a polydimethylsiloxane polymer having an aminoethyl aminopropyl side chain.

The aminosilicone polymer may conform to the formula:

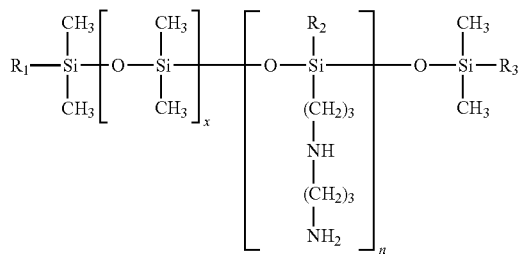

in which n and m are integers such that the weight average molecular weight is between 10,000 Dalton and 60,000 Dalton, $R_1$ and $R_3$ are independently selected from —OH or —OCH$_3$; $R_2$ is H or a $C_1$ to $C_3$ alkyl, or methyl or H, preferably methyl. "n" may be on average from 1 to 50, or from 5 to 20, or from 6 to 10, or from 8 to 9, and "m" may be on average from 120 to 300, or from 150 to 200. "n" may be on average from 5 to 8, "m" may be on average from 150 to 180, $R_1$ and $R_3$ may be both methyl, and $R_3$ may be —OCH$_3$.

The aminosilicone polymer may have an amine number of from 0.1 meq/g to 3 meq/g, or from 0.7 meq/g to 2.5 meq/g, or from 0.6 meq/g to 1 meq/g.

Suitable example aminosilicone polymers can be found in the following patent documents, which are incorporated herein by reference: Decoster U.S. Pat. No. 6,451,747B1 col. 17, 1.4-27; Hughes U.S. Pat. No. 5,567,428 col. 13, 1.40-56; Gawtrey et al US2004/0010863A1, § 0016 to § 0039; Mahr et al US2006/0041026A1.

The composition A may comprise from 1% to 15%, or from 1.5% to 5%, of an aminosilicone polymer. The viscosity of the aminosilicone polymer may be from 10 to 100,000 mPa·s, or from 100 to 10,000 mPa·s.

Silicone Resin

The silicone resin may be an MQ resin. "M" stands for Me$_3$SiO and "Q" stands for SiO$_4$. The MQ resin may have an M:Q molar ratio of from 0.5:1.0 to 1.5:1.0. The weight average molecular weight of the resin may be from 1000 Daltons to 10,000 Daltons. The MQ resin may contain at least 80 mol. %, or at least 95 mol. %, of units of the general formulae below:

$$R^7{}_3SiO_{1/2}$$

$$SiO_{4/2}$$

in which $R^7$ is $C_{1-40}$ alkyl, H, —OR or —OH radicals. The ratio of the units of the general formulae may be from 0.5 to 2.0, or from 0.5 to 1.5. The not more than 3% by weight, or not more than 2.5% by weight, of the radicals $R^7$ may be —OR and —OH.

The remaining units of the MQ silicone resin may be units of the following general formulae;

$$R^7{}_2SiO_{2/2}$$

$$R^7SiO_{1/2}$$

in which $R^7$ is $C_{1-40}$ alkyl, H, —OR or —OH radicals.

$R^7$ may be $C_{1-40}$ alkyl that is optionally halogen-substituted, linear, cyclic, branched, aromatic, saturated or unsaturated. $R^7$ may be an alkyl group having $C_{1-6}$ carbon atoms, or a phenyl radical. The halogen substituents may be selected from fluorine and chlorine. $R^7$ may be selected from methyl, ethyl, phenyl and H. The composition may comprise from 0.1% to 10%, or from 1% to 5%, or from 2% to 4% of a MQ resin.

MQ resins are available from Wacker-Chemie AG, D-81737 München, Germany. For example, MQ-RESIN POWDER 803 TF is a co-hydrolysis product of tetraalkoxy silane (Q unit) and trimethyl-ethoxy silane (M unit) and can be seen as a three dimensional network of polysilicic acid units which are endblocked with trimethylsilyl groups. Some residual ethoxy and hydroxy functions are present. MQ resins are also available from Dow Corning. For example, Dow Corning® MQ-1640 Flake Resin is a combination of MQ and T propyl silicone resin and has the INCI name: Trimethylsiloxy silicate (and) Polypropyl silsesquioxane.

Ether of a Water-Soluble Polyhydric Alcohol

The composition A may further comprise an ether of a water-soluble polyhydric alcohol. The ether of a water-soluble polyhydric alcohol has the advantage that it is able to prevent the aminosilicone and the silicone resin from forming a complex in the case that both are comprised in composition A. The ether of a water-soluble polyhydric alcohol may be a non-polymeric, amphiphilic compound. Indeed, the aminosilicone comprises amino side chains, which lend hydrophilic character to the aminosilicone, and the silicone resin typically is hydrophobic in nature. Thus where the ether of a water-soluble polyhydric alcohol has amphiphilic chemistry it can interact with both the aminosilicone and the silicone resin and keep them from clumping, and also from precipitating. The composition A may comprise ether of a water-soluble polyhydric alcohol, wherein the ether of a water-soluble polyhydric alcohol is selected from the group consisting of diethyleneglycol monobutylether, ethylene glycol monohexyl ether, and a mixture of diethyleneglycol monobutylether and ethylene glycol monohexyl ether. The composition A may comprise from 0.01% to 20%, or from 0.1% to 10%, or from 0.5% to 5%, or from 1.0% to 5%, or from 2% to 5% ether of a water-soluble polyhydric alcohol.

A suitable product for use in the present invention is available under the trade mark Wacker®/BELSIL ADM 8301 E by the company Wacker-Chemie AG, D-81737 München, Germany. This product contains from 10% to 20% of poly[3-((2-aminoethyl)amino)propyl]methyl(dimethyl)siloxane, hydroxyterminated, which is an aminosilicone. It also contains from 0.1% to 0.2% octamethylcyclotetrasiloxane and from 1% to 5% of an MQ silicone resin. The product also contains from 1% to 3% ethylene glycol monohexyl ether and from 5% to 10% diethyleneglycol monobutylether. Said product is described in US2006/0041026A1 which is incorporated herein by reference. A similar product is Wacker® HC303 also from Wacker-Chemie AG.

Cationic Polymer(s)

The composition A may further comprise one or more cationic polymer(s). The cationic polymer(s) may be identical to those which have been described hereinbefore in the context of the shell of the core-shell pigment(s). The cationic polymer(s) may typically be selected from the group consisting of polyethyleneimine, polyallylamine hydrochloride, polydiallyldimethylammonium chloride, polyvinylamine, copolymers thereof and mixtures thereof. The cationic polymer(s) may preferably be selected from the group consisting of polyethyleneimine, polydiallyldimethylammonium chloride, copolymers thereof and mixtures thereof.

LbL (Layer-by-Layer) Coating of the Hair: Step B)

The method according to the present invention may further comprise, prior to step A), step B) of providing in at least a second portion of the hair one or more polymeric sublayer(s). The first and second portions of the hair have at least one first common area. Having at least one common area (common region) between the first portion of the hair and the second portion of the hair ensures that at least a portion of the composition A comprising one or more pigment(s) is applied to the same portion of the hair as at least a portion where the one or more polymeric sublayer(s) are positioned on the hair. Step B) enhances the adhesion between the hair and the pigment(s) since the polymeric sublayer(s) positioned on the hair more or less function as "glue" between the hair and the pigment(s).

Step B) is carried out prior to step A). Step B) may be carried out immediately prior to step A), or at least 1 hour prior to step A), or at least 24 hours prior to step A), or at least 10 days prior to step A), or at least one month prior to step A).

Step B1)

Step B) may comprise:
B1) applying a composition B1 comprising one or more cationic polymer(s) to the second portion of the hair.

Composition B1

The composition B1 may be applied to the second portion of the hair, or may be applied all over the hair.

The composition B1 may be applied in one go or step-by-step to the hair. The composition B1 may be applied step-by-step, for example in case the hair is damaged. Applying the composition B1 step-by-step, may help to ensure that the hair is saturated with the composition B1 and may therefore provide a better coverage of the hair with the composition B1.

Cationic Polymer(s)

The composition B1 comprises one or more cationic polymer(s).

The cationic polymer(s) may be coloured.

The cationic polymer(s) may preferably be uncoloured.

The cationic polymer(s) may comprise one or more amino functional group(s) per polymer chain, wherein the amino functional group(s) are selected from the group consisting of primary, secondary, tertiary, quaternary amino functional groups and mixtures thereof, preferably from the group consisting of secondary, tertiary, quaternary amino functional groups and mixtures thereof, more preferably from quaternary amino functional groups.

The cationic polymer(s) may be selected from the group consisting of polyethyleneimine, polyallylamine hydrochloride, polydiallyldimethylammonium chloride, polyvinylamine, copolymers thereof and mixtures thereof. The cationic polymer(s) may preferably be selected from the group consisting of polyethyleneimine, polydiallyldimethylammonium chloride, copolymers thereof and mixtures thereof.

The copolymers may be random or block copolymers.

The cationic polymer(s) may be linear or branched.

The cationic polymer(s) may be selected from the group consisting of:

a) Linear polyethyleneimine of the formula:

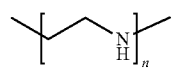

in which n is an integer representing the degree of polymerization, wherein n ranges from 50 to 20,000, alternatively from 100 to 3,500;

b) Branched polyethyleneimine consisting of primary, secondary and tertiary amine groups of the formula:

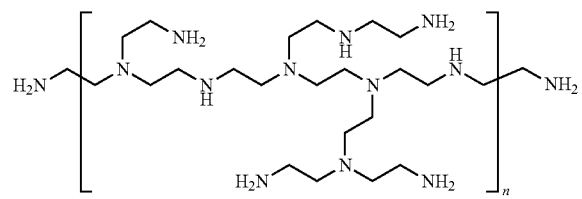

in which n is an integer representing the degree of polymerization, wherein n ranges from 5 to 4,000, alternatively from 50 to 500;

c) Polyallylamine hydrochloride of the formula:

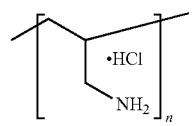

in which n is an integer representing the degree of polymerization, wherein n ranges from 50 to 20,000, alternatively from 150 to 2000;

d) Polydiallyldimethylammonium chloride of the formula:

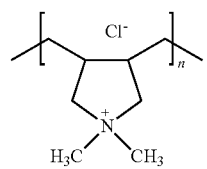

in which n is an integer representing the degree of polymerization, wherein n ranges from 10 to 20,000, alternatively from 150 to 4,000;

copolymers thereof and mixtures thereof.

The copolymers may be random or block copolymers.

The cationic polymer(s) may have a charge density at full protonation of at least 0.3, preferably at least 0.6, more preferably at least 0.8, even more preferably at least 1.0 positive charges per monomer unit.

The cationic polymer(s) may have a weight average molecular weight of more than 0.5 kD, preferably from 0.5 kD to 5000 kD, more preferably from 2 kD to 1000 kD, even more preferably from 10 kD to 200 kD, most preferably from 25 kD to 70 kD.

Step B2)

Step B) may further comprise:

B2) applying a composition B2 comprising one or more anionic polymer(s) to the second portion of the hair after step B1).

By carrying out step B2), a first polymeric layer made of an anionic polymeric sublayer positioned on top of a cationic polymeric sublayer is obtained in the first common area (first common region) of the hair after the successive application of the cationic polymer(s) and the anionic polymer(s). Hair is naturally negatively charged. Therefore, the inner sublayer of the coated hair which is positively charged can easily attach to the surface of the hair and the outer sublayer of the coated hair which is negatively charged can easily attach to the surface of the cationic polymeric sublayer positioned underneath. Since the outer sublayer of the coated hair has an electrostatic structure similar to the one of the outer layer of natural hair, it is possible to apply any further hair treatment on top of the first polymeric layer that would usually be directly applied onto hair.

While not wishing to be bound by theory, it is believed that having at least one common area between the first portion of the hair and the second portion of the hair ensures that the composition A comprising the pigment(s) enters into contact with the first polymeric layer made of the cationic and anionic sublayer(s) and is thereby attached to the hair in a stable and durable manner.

Step B2) is carried out after step B1). Step B2) may be carried out immediately after step B1), or at least 1 hour after step B1), or at least 24 hours after step B1), or at least 10 days after step B1), or at least one month after step B1).

Composition B2

The composition B2 may be applied all over the hair.

The composition B2 is applied after the composition B1 to the hair.

The composition B2 may be applied in one go or step-by-step to the hair. The composition B2 may be applied step-by-step, for example in case the hair is damaged. Applying the composition B2 step-by-step, may help to ensure that the hair is saturated with the composition B2 and may therefore provide a better coverage of the hair with the composition B2.

Anionic Polymer(s)

The second composition comprises one or more anionic polymer(s).

The anionic polymer(s) may be coloured.

The anionic polymer(s) may preferably be uncoloured.

The anionic polymer(s) may comprise one or more functional group(s) per polymer chain selected from the group consisting of phenyl group, alkyl groups comprising at least 8 carbon atoms and mixtures thereof.

The anionic polymer(s) may be selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof. The anionic polymer(s) may preferably be selected from the group consisting of polystyrene sulfonate salts, polystyrene sulfonate/polystyrene copolymer salts, copolymers thereof and mixtures thereof.

The copolymers may be random or block copolymers.

The anionic polymer(s) may be linear or branched.

The anionic polymers may be selected from the group consisting of:

a) Polystyrene sulfonate (PSS) sodium salt of the formula:

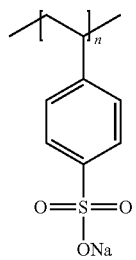

in which n is an integer representing the degree of polymerization, wherein n ranges from 50 to 20,000, alternatively from 150 to 2500;

b) Co-polymer of polystyrene sulfonate (PSS) sodium salt and poly(4-styrenesulfonic acid-co-maleic acid) of the formula:

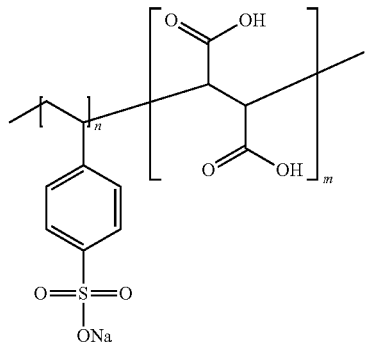

in which n and m are integers representing the degree of polymerization, wherein n+m ranges from 50 to 20,000, alternatively from 150 to 2500;

c) λ-Carrageenan;

d) Dextran sulfate sodium salt;

e) Polyacrylic acid (PAA) of the formula:

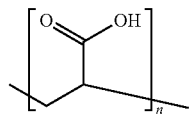

in which n is an integer representing the degree of polymerization, wherein n ranges from 50 to 20,000, alternatively from 150 to 1,000;
f) Alginic acid sodium salt;
g) Carboxymethylcellulose sodium salt of the formula:

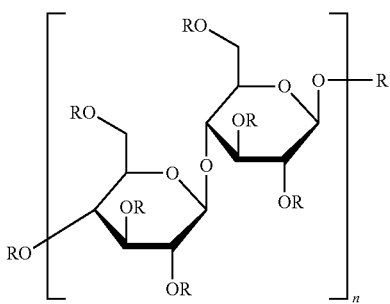

in which:
R is H or $(CH_2)_2COONa$ and
n is an integer representing the degree of polymerization; copolymers thereof and mixtures thereof.

The copolymers may be random or block copolymers.

The anionic polymer(s) may have a charge density at full deprotonation of at least 0.3, alternatively at least 0.6, alternatively at least 0.8, alternatively at least 1.0 negative charges per monomer unit.

The anionic polymer(s) may have a weight average molecular weight of at least 1 kD, alternatively from 10 kD to 1000 kD, alternatively from 70 to 500 kD.

Compositions B1 and B2

The cationic polymer(s) and the anionic polymer(s) may preferably be uncoloured. The hair portions onto which compositions B1 and B2 are applied may be the same. The compositions B1 and B2 may be applied all over the hair.

Repeating Steps

In the event that step B2) is carried out, the method may further comprise, after step B2), repeating steps B1) and B2) at least once. Preferably, steps B1) and B2) may be repeated once, twice, three times or four times. Repeating steps B1) and B2) ensures that at least one additional polymeric layer made of an anionic polymeric sublayer and a cationic polymeric sublayer is positioned on top of the first polymer layer made of the cationic polymer(s) of the composition B1 and the anionic polymer(s) of the composition B2. In the case that composition A also comprises cationic polymer(s), steps B1) and B2) are repeated at least once. This ensures that the uppermost sublayer of polymeric layers onto which the cationic polymer(s) of the composition A can be attached is negatively charged.

In the event that step B2) is carried out, the method may further comprise after step B2) (and preferably after each of the repeated steps B2)), repeating step B1) once. Repeating step B1) once ensures that the uppermost surface of the treated hair portion is formed by a cationic polymeric sublayer, and as such, that the uppermost surface of the treated hair portion is positively charged.

Final Hair Colouring Step: Step C)

The method according to the present invention may further comprise, after step A), step C) of colouring the hair by applying hair colouring composition(s) to at least a third portion of the hair. The third portion of the hair has at least a common area (common region) with the first portion of the hair, and preferably also with the second portion of hair. As such, the third portion of the hair has at least a second common area (second common region) with the first common area (first common region). Having at least one common area (common region) between the third portion and the first portion ensures that at least a portion of the composition A comprising one or more pigment(s) is applied to the same portion of the hair where colouring is carried out. The hair colouring composition(s) may comprise coloured polymer(s). The hair colouring composition(s) may form coloured layer(s) after application onto the hair.

Step C) is carried out after step A). Step C) may be carried out immediately after step A), or at least 1 hour after step A), or at least 24 hours after step A), or at least 10 days after step A), or at least one month after step A).

Step C1)

Step C) may comprise
C1) applying a composition C1 comprising one or more cationic polymer(s) to the third portion of the hair, wherein the cationic polymer(s) may be cationic coloured polymers.

Composition C1)

The composition C1 may be applied to the third portion of the hair, or may be applied all over the hair.

The composition C1 may be applied in one go or step-by-step to the hair. The composition C1 may be applied step-by-step, for example in case the hair is damaged. Applying the composition C1 step-by-step, may help to ensure that the hair is saturated with the composition C1 and may therefore provide a better coverage of the hair with the composition C1.

Cationic Polymer(s)

As explained hereinbefore, the composition C1 may comprise one or more cationic polymer(s). The cationic polymer(s) may be selected from the group consisting of cationic coloured polymers, cationic uncoloured polymers and mixtures thereof.

The cationic polymer(s) may comprise one or more monomer unit(s) comprising one or more amino functional group(s). The amino functional group(s) may be selected from the group consisting of primary, secondary, tertiary, quaternary amino functional groups and mixtures thereof. The amino functional group(s) may preferably be selected from the group consisting of primary, secondary amino functional groups and mixtures thereof. The amino functional group(s) may more preferably be selected from secondary amino functional groups.

The cationic polymer(s) may have a charge density at full protonation of at least 0.3, preferably at least 0.6, more preferably at least 0.8, even more preferably at least 1.0 positive charges per monomer unit.

The cationic polymer(s) may have a weight average molecular weight of more than 0.5 kD, preferably from 0.5 kD to 5000 kD, more preferably from 2 kD to 1000 kD, even more preferably from 10 kD to 200 kD, most preferably from 25 kD to 70 kD.

The cationic polymer(s) may be selected from the group consisting of polyethyleneimine, polyallylamine hydrochloride, polyvinylamine, polydiallyldimethylammonium chloride, copolymers thereof and mixtures thereof.

The copolymers may be random or block copolymers.

The cationic polymer(s) may be linear or branched.

The cationic polymer(s) may be selected from the group consisting of:
a) Linear polyethyleneimine of the formula:

in which n is an integer representing the degree of polymerization, wherein n ranges from 50 to 20,000, alternatively from 100 to 3,500;

b) Branched polyethyleneimine consisting of primary, secondary and tertiary amine groups of the formula:

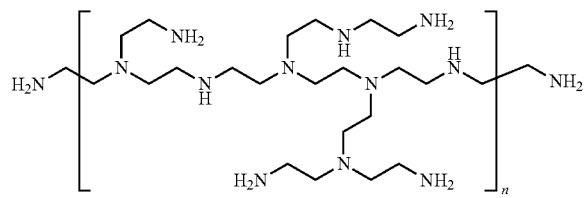

in which n is an integer representing the degree of polymerization, wherein n ranges from 5 to 4,000, alternatively from 50 to 500, c) Polyallylamine hydrochloride (PAH) of the formula:

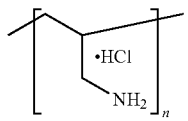

in which n is an integer representing the degree of polymerization, wherein n ranges from 50 to 20,000, alternatively from 150 to 2000;

d) Polydiallyldimethylammonium chloride (PDADMAC) of the formula:

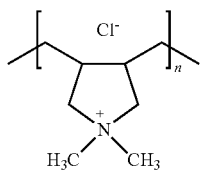

in which n is an integer representing the degree of polymerization, wherein n ranges from 10 to 20,000, alternatively from 150 to 4,000;

copolymers thereof and mixtures thereof.

The copolymers may be random or block copolymers.

Step C2)

Step C) may comprise

C2) applying a composition C2 comprising one or more anionic polymer(s) to the third portion of the hair.

By carrying out step C2), a polymeric layer made of an anionic polymeric sublayer positioned on top of a cationic polymeric sublayer may be obtained in the second common area (second common region) after the successive application of the cationic polymer(s) and the anionic polymer(s).

Step C2) is preferably carried out after step C1). Step C2) may be carried out immediately after step C1), or at least 1 hour after step C1), or at least 24 hours after step C1), or at least 10 days after step C1), or at least one month after step C1). However, in the case that composition A also comprises cationic polymer(s) as described hereinbefore, step C2) is carried out first, optionally followed by carrying out step C1), and further optionally by repeating steps C2) and C1) as described in more detail below.

Composition C2

The composition C2 may be applied to the third portion of the hair, or may be applied all over the hair.

The composition C2 may be applied in one go or step-by-step to the hair. The composition C2 may be applied step-by-step, for example in case the hair is damaged. Applying the composition C2 step-by-step, may help to ensure that the hair is saturated with the composition C2 and may therefore provide a better coverage of the hair with the composition C2.

Anionic Polymer(s)

The anionic polymer(s) which are comprised in the composition C2 may be selected from the group consisting of anionic coloured polymers, anionic uncoloured polymers and mixtures thereof.

The anionic polymer(s) may have a charge density at full deprotonation of at least 0.3, preferably at least 0.6, more preferably at least 0.8, even more preferably at least 1.0 negative charges per monomer unit.

The anionic polymer(s) may have a weight average molecular weight of at least 1 kD, preferably from 10 kD to 1000 kD, more preferably from 70 kD to 500 kD.

The anionic polymer(s) may comprise one or more monomer unit(s) comprising one or more functional group(s) selected from the group consisting of sulfate, sulfonate, carboxylate, phosphate, phosphonate groups and mixtures thereof. The functional group(s) may preferably be selected from the group consisting of sulfate, sulfonate, carboxylate groups and mixtures thereof.

The anionic polymer(s) may be selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof. The salts may be sodium salts.

The copolymers may be random or block copolymers.

The anionic polymer(s) may be selected from the group consisting of:

a) Polystyrene sulfonate (PSS) sodium salt of the formula:

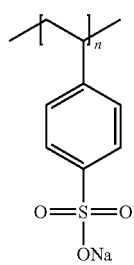

in which n is an integer representing the degree of polymerization, wherein n ranges from 50 to 20,000, alternatively from 150 to 500;

b) Co-polymer of polystyrene sulfonate (PSS) sodium salt and poly(4-styrenesulfonic acid-co-maleic acid) of the formula:

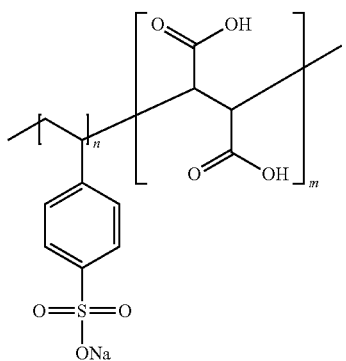

in which n and m are integers representing the degree of polymerization, wherein n+m ranges from 50 to 20,000, alternatively from 150 to 2500;
c) λ-Carrageenan;
d) Dextran sulfate sodium salt;
e) Polyacrylic acid (PAA) of the formula:

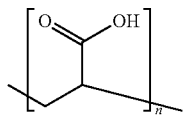

in which n is an integer representing the degree of polymerization, wherein n ranges from 50 to 20,000, alternatively from 150 to 5000;
f) Alginic acid sodium salt;
g) Carboxymethylcellulose sodium salt of the formula:

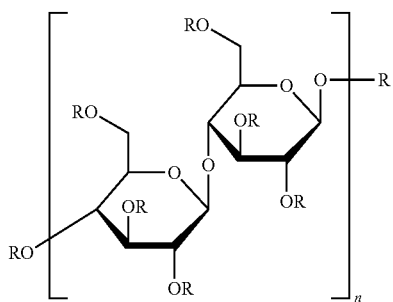

in which:
R is H or $(CH_2)_2COONa$ and
n is an integer representing the degree of polymerization;
copolymers thereof and mixtures thereof.

The copolymers may be random or block copolymers.

Compositions C1 and C2

At least one of the cationic polymer(s) and the anionic polymer(s) may preferably be coloured. The hair portions onto which compositions C1 and C2 are applied may be the same. The compositions C1 and C2 may be applied all over the hair.

Repeating Steps

In the event that step C2) is carried out, the method may further comprise, after step C2), repeating steps C1) and C2) at least once. Preferably, steps C1) and C2) may be repeated once, twice, three times or four times. Repeating steps C1) and C2) ensures that at least one additional polymeric layer made of an anionic polymeric sublayer and a cationic polymeric sublayer is positioned on top of the first polymer layer made of the cationic polymer(s) of the composition C1 and the anionic polymer(s) of the composition C2.

In the event that step C2) is carried out, the method may further comprise after step C2) (and preferably after each of the repeated steps C2)), repeating step C1) once. Repeating step C1) once ensures that the uppermost surface of the treated hair portion is formed by a cationic polymeric sublayer, and as such, that the uppermost surface of the treated hair portion is positively charged.

Cationic Coloured Polymers and Anionic Coloured Polymers

The cationic polymers and the anionic polymers used in the present invention, and preferably used in step C) as defined hereinbefore may comprise at least one chromophore and/or at least one fluorophore. Any of the hereinbefore exemplified cationic polymers or anionic polymers can comprise at least one chromophore and/or at least one fluorophore either in the skeleton or as pendent group.

The chromophores may be selected from the group consisting of nitrobenzene, azo, imine, hydrazine, phenothiazine, xanthene, phenanthridine, phthalocyanin and triarylmethane-based dyes, derivatives thereof, derivatives obtained from direct dyes containing a carbonyl group and mixtures thereof. The chromophores may be selected from the group consisting of acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, derivatives thereof and mixtures thereof.

The chromophores may be substituted with at least one amine, hydroxyl, sulfate, sulfonate, carboxylate, phosphate, phosphonate, or halide group. These chromophores may be selected from the group consisting of derivatives of acidic nitro direct dyes, acidic azo dyes, acidic azine dyes, acidic triarylmethane dyes, acidic indoamine dyes and non-quinone acidic natural dyes, and mixtures thereof.

The chromophores may also be selected from derivatives of any of the direct dyes exemplified in the direct dyes section of this application.

The fluorophores may be selected from the group consisting of derivatives from di-, tetra- or hexa-sulfonated triazine-stilbenes, coumarins, imidazolines, diazoles, triazoles, benzoxazolines, biphenyl-stilbenes optical brighteners, and mixtures thereof.

A cationic coloured polymer or an anionic coloured polymer may comprise the same type of chromophore and/or fluorophore or different types of chromophores and/or fluorophores. Having a cationic coloured polymer or an anionic coloured polymer with different types of chromophores and/or fluorophores may help to cover a broad range of colour shades which can be obtained on hair which are coloured according to the method of the present wherein the composition A or the second composition comprises such a cationic coloured polymer or such an anionic coloured polymer.

The cationic coloured polymers may be selected from the group consisting of:

i. Coloured linear or branched polyethyleneimine (PEI) of the formula:

in which n and m are integers representing the degree of polymerization, wherein m/n ranges from 0 to 1,000 provided that n is different from 0 and/or m+n ranges from 50 to 20,000, alternatively from 100 to 3,500;

ii. Coloured polyallylamine of the formula:

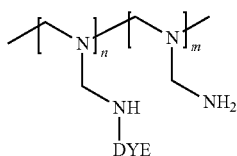

in which n and m are integers representing the degree of polymerization, wherein m/n ranges from 0 to 1,000 provided that n is different from 0 and/or m+n ranges from 50 to 20,000, alternatively from 150 to 2000;

iii. Coloured polydiallyldimethylammonium chloride of the formula:

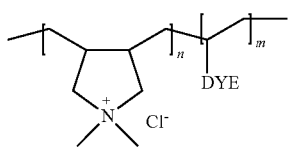

in which n and m are integers representing the degree of polymerization, wherein m/n ranges from 0 to 1,000 provided that n is different from 0 and/or m+n ranges from 10 to 20,000, alternatively from 100 to 4000;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

The cationic coloured polymers may be selected from linear polyethyleneimine (PE)—Rhodamine B of the formula:

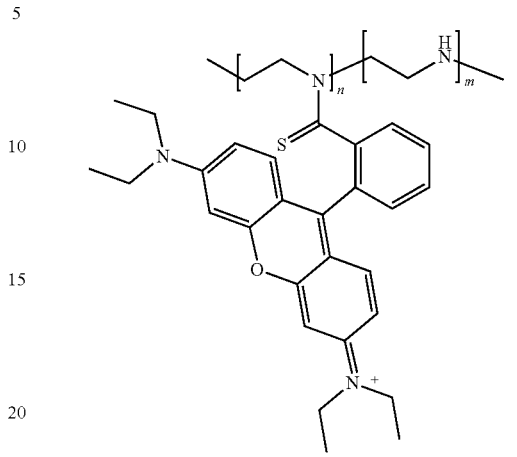

in which n and m are integers representing the degree of polymerization, wherein m/n may range from 0 to 1,000 provided that n is different from 0 and/or m+n may range from 50 to 20,000, alternatively from 100 to 3,500. These polymers may be block copolymers or random copolymers.

The anionic coloured polymers may be selected from anionic coloured polymers with the following formula:

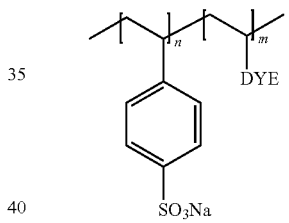

in which n and m are integers representing the degree of polymerization, wherein m/n may range from 0 to 1,000 provided that n is different from 0 and/or m+n may range from 50 to 20,000, alternatively from 150 to 500;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

Additional Steps

Removal of the Excess of the Compositions

At least one of steps A), B1), B2), C1) and C2) preferably all the steps A), B1), B2), C1) and C2) may further comprise the subsequent sub-step of removing the excess of the respective composition(s) with fingers and/or a towel.

Application of Energy

At least one of steps A), B1), B2), C1) and C2), preferably all the steps A), B1), B2), C1) and C2) may further comprise the subsequent sub-step of applying energy to the hair in the form of heat, ultrasounds, infrared and/or microwaves. This sub-step may be carried out either after the application of the respective composition to the hair or after removing the excess of the respective composition from the hair. While not wishing to be bound by theory, it is believed that applying energy to the hair may e.g., accelerate the speed of formation of the polymeric sublayers on the hair and therefore may increase the stability of the sublayers once they are formed on the hair in step B). The hair may be heated to a temperature ranging from 5° C. to 70° C., alternatively 20° C. to 60° C., alternatively 40° C. to 60° C.

Washing and/or Rinsing

At least one of A), B1), B2), C1) and C2), preferably all the steps A), B1), B2), C1) and C2) may further comprise the subsequent sub-step of washing and/or rinsing the hair, preferably with a liquid selected from the group consisting of a cosmetically acceptable solvent, a solution comprising a cosmetically acceptable solvent and a cosmetically acceptable salt, a shampoo composition and mixtures thereof, more preferably with water.

Pre-Treatment

The hair may be pretreated prior to step B1) to modify the number of positive or negative charges in some portions of the hair or all over the hair. This pretreatment may be done using chemical or physical means such as pH change, oxidation, reduction, bleaching, plasma treatment, ozone treatment, electrowetting, dry or wet ion-treatment.

Compositions A, B1, B2, C1 and C2

Solvents

Each of the compositions A, B1, B2, C1 and C2 which are used to carry out the method according the present invention may further comprise at least one solvent. The solvent may be selected from water, or a mixture of water and at least one organic solvent to dissolve the compounds that would not typically be sufficiently soluble in water. Each of the compositions A, B1, B2, C1 and C2 may be aqueous solutions.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

Typically, each of the compositions A, B1, B2, C1 and C2 may comprise water as a main ingredient, particularly in a total amount ranging from at least 50%, alternatively from at least 60%, alternatively from at least 70%, by total weight of the composition. Typically, when present, the compositions comprise a total amount of organic solvents ranging from about 1% to about 30%, by total weight of the composition.

Concentrations

Each of the compositions B1 and C1 may comprise a total concentration of cationic polymers which is ranging from 0.1 g/L to 100 g/L, alternatively from 0.5 g/L to 100 g/L, alternatively from 2 g/L to 50 g/L, alternatively from 5 g/L to 10 g/L.

Each of the compositions B2 and C2 may comprise a total concentration of anionic polymers which is ranging from 0.1 g/L to 100 g/L, alternatively from 0.5 g/L to 100 g/L, alternatively from 2 g/L to 50 g/L, alternatively from 5 g/L to 10 g/L.

Salt

Each of the compositions A, B1, B2, C1 and C2 may comprise at least one cosmetically acceptable salt at a concentration ranging from 0 to 1.5 mol/L, preferably from 0.05 to 1 mol/L, more preferably from 0.2 to 0.5 mol/L.

The cosmetically acceptable salt may be selected from the group consisting of an organic salt, a mineral salt and mixture thereof. The organic salt may be sodium citrate. The mineral salt may be selected from the group consisting of sodium chloride, ammonium sulfate, magnesium chloride, calcium chloride and mixtures thereof. The cosmetically acceptable salt may be sodium chloride.

Applicators

Each of the compositions A, B1, B2, C1 and C2 may be applied to the hair using an applicator such as a brush or a sponge. Alternatively, all composition may be applied to the hair by spraying or foaming the each of the compositions A, B1, B2, C1 and C2 to the hair or by dipping the hair into the compositions A, B1, B2, C1 and/or C2. Alternatively, each of the compositions A, B1, B2, C1 and C2 may be applied to the hair using printing technology.

Other Ingredients

Each of the compositions A, B1, B2, C1 and C2 according to the present invention may comprise, in addition to the ingredients indicated above, further ingredients in order to further enhance the properties of the composition, as long as these are not excluded by the claims.

Suitable further ingredients include, but not limited to: alkalizing agents; oxidative dye precursors, direct dyes; chelants; radical scavengers; pH modifiers and buffering agents; thickeners and/or rheology modifiers; carbonate ion sources; peroxymonocarbonate ion sources; surfactants; polymers; fragrances; enzymes; dispersing agents; peroxide stabilizing agents; antioxidants; natural ingredients (such as proteins, protein compounds, and plant extracts), conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Alkalizing Agents

Each of the compositions A, B1, B2, C1 and C2 according to the present invention may further comprise at least one alkalizing agent. Any alkalizing agent known in the art may be used.

Typically, each of the compositions A, B1, B2, C1 and C2 may comprise a total amount of alkalizing agents ranging from 0.1% to 10%, alternatively from 0.5% to 6%, alternatively from 1% to 4%, by total weight of the composition.

Alternatively, each of the compositions A, B1, B2, C1 and C2 may comprise a total amount of alkalizing agents of less than 1%, preferably less than 0.5%, more preferably less than 0.3%, even more preferably less than 0.1% by total weight of the composition. Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine.

Each of the compositions A, B1, B2, C1 and C2 may comprise a total amount of ammonia of less than 1%, preferably less than 0.5%, more preferably less than 0.3%, even more preferably less than 0.1% by total weight of the composition. Each of the compositions A, B1, B2, C1 and C2 may most preferably be free of ammonia. These embodiments are particularly interesting since such compositions are low odour compositions.

Preferably, if present, the ammonium ions and carbonate ions are present in the composition at a weight ratio of from 3:1 to 1:10, alternatively from 2:1 to 1:5.

When the compositions of the present invention is obtained by mixing a developer and a tint composition prior to use, the alkalizing agent is generally present in the tint composition.

Oxidative Dye Precursors

Each of the compositions A, B1, B2, C1 and C2 according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, each of the compositions A, B1, B2, C1 and C2 may comprise a total amount of oxidative dye precursors ranging up to 12%, preferably from 0.1% to 10%, more preferably from 0.3% to 8%, even more preferably from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminoethane, 2-[(3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the compositions of the invention are obtained by mixing a tint composition and a developer composition, the primary intermediates and couplers are usually incorporated into the tint composition.

Direct Dyes

Each of the compositions A, B1, B2, C1 and C2 according to the present invention may further comprise compatible direct dyes, in an amount sufficient to provide additional colouring, particularly with regard to intensity. Typically, each of the compositions A, B1, B2, C1 and C2 may comprise a total amount of direct dyes ranging from about 0.05% to about 4%, by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethyl amino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline. HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the compositions are obtained by mixing a tint composition and a developer composition, the direct dyes are usually incorporated into the tint composition.

Chelants

Each of the compositions A, B1, B2, C1 and C2 according to the present invention may further comprise at least one chelant (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, each of the compositions A, B1, B2, C1 and C2 may comprise a total amount of chelants ranging from at least 0.01%, preferably from 0.01% to 5%, more preferably from 0.25% to 3%, even more preferably from 0.5% to 1%, by total weight of the composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative —$PO_3R_2$, wherein $R_2$ is a $C_1$ to $C_6$ alkyl or aryl group and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N''-ethylenediamine diacetic acid, their salts thereof, their derivatives thereof, and mixtures thereof.

In a specific embodiment, each of the compositions A, B1, B2, C1 and C2 may comprise a chelant selected from the group consisting of diethylenetriamine-N,N',N'''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof, alternatively ethylenediaminedisuccinic acid (EDDS).

When the compositions of the invention are obtained by mixing a tint composition and a developer composition, the chelants may be incorporated in the tint composition and/or in the developer composition. A chelant is usually present in the developer composition for stability reason.

Radical Scavengers

Each of the compositions A, B1, B2, C1 and C2 according to the present invention may further comprise at least one radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring/bleaching process.

Typically, each of the compositions A, B1, B2, C1 and C2 may comprise a total amount of radical scavengers ranging from 0.1% to 10%, preferably from 1% by weight to 7%, by total weight of the composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof, alternatively glycine, sarcosine, lysine, serine, 2 methoxyethylamine, glucosamine, glutamic acid, morpholine, piperadine, ethylamine, 3 amino-1-propanol, and mixtures thereof. As used herein, the term "salts thereof"—in the context of radical scavengers—means particularly potassium salts, sodium salts, ammonium salts, and mixtures thereof.

pH Modifiers and Buffering Agents

Each of the compositions A, B1, B2, C1 and C2 according to the present invention may further comprise, in addition to the alkalizing agent discussed above, a pH modifier and/or buffering agent.

Suitable pH modifiers and/or buffering agents include, but are not limited to: ammonia; alkanolamines (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

Each of the compositions A, B1, B2, C1 and C2 according to the invention may further comprise at least one thickener in an amount sufficient to provide the compositions with a viscosity so that it can be readily applied to the hair without unduly dripping off the hair and causing mess.

Typically, each of the compositions A, B1, B2, C1 and C2 may comprise a total amount of thickeners ranging from at least 0.1%, preferably at least 0.5%, more preferably at least 1%, by total weight of the composition.

Suitable thickeners include, but are not limited to: associative polymers, polysaccharides, non-associative polycarboxylic polymers, and mixtures thereof.

Carbonate Ion Sources

Each of the compositions A, B1, B2, C1 and C2 according to the present invention may further comprise at least one source of carbonate ions, carbamate ions, hydrogen carbonate ions, and mixtures thereof in a sufficient amount to reduce damage to the hair during the colouring process.

Typically, each of the compositions A, B1, B2, C1 and C2 may comprise a total amount of a carbonate ion source ranging from 0.1% to 15%, preferably from 0.1% to 10%, more preferably from 1% to 7%, by total weight of the composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

Each of the compositions A, B1, B2, C1 and C2 according to the present invention may further comprise at least one conditioning agent, and/or be used in combination with a composition comprising at least one conditioning agent.

Typically, each of the compositions A, B1, B2, C1 and C2 may comprise a total amount of conditioning agents ranging from 0.05% to 20%, preferably from 0.1% to 15%, more preferably from 0.2% to 10%, even more preferably from 0.2% to 2%, most preferably from 0.5% to 2%, by total weight of the composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Surfactant(s)

Each of the compositions A, B1, B2, C1 and C2 according to the present invention may further comprise one or more surfactant(s).

Typically, each of the compositions A, B1, B2, C1 and C2 composition may comprise a total amount of surfactants ranging from 0.1% to 30%, preferably from 2% to 30%, more preferably from 8% to 25%, even more preferably from 10% to 20%, by total weight of the composition.

Each of the compositions A, B1, B2, C1 and C2 may comprise one or more surfactant(s) selected from the group consisting of anionic surfactants, amphoteric surfactants, nonionic surfactants and mixtures thereof. Each of the compositions A, B1, B2, C1 and C2 may comprise a total amount of anionic surfactants ranging from 0.1% to 20%, preferably from 0.1% to 15%, more preferably from 5% to 15%, by total weight of the compositions; and a total amount of amphoteric and/or nonionic components, which may range independently from each other from 0.1% to 15%, preferably from 0.5% to 10%, more preferably from 1% to 8%, by total weight of the compositions.

Ionic Strength

Each of the compositions A, B1, B2, C1 and C2 of the present invention may further have an ionic strength as defined herein of less than 1.35 mole/kg, preferably from 0.10 to 0.75 mole/kg, more preferably from 0.20 to 0.60 mole/kg. Whilst not being bound by theory, it is believed that the ionic strength value may also affect the resultant viscosity and root adhesion properties of the composition. The ionic strength can be affected by salt resources such as the dyes, sodium sulphate, ammonium carbonate anti-oxidants and chelants such as EDDS. The dye tends to have the greatest effect on the ionic strength and thus the amounts added in order to provide any particular shade need to be considered in terms of ionic strength as well as dye outcome in order to prevent viscosity and root adhesion problems.

The ionic strength of the compositions is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: $I=\frac{1}{2}((2\times(+1)^2\times 0.050)+(+1)^2\times 0.020+(-2)^2\times 0.050+(-1)^2\times 0.020)=0.17$ M.

Foam

Each of the compositions A, B1, B2, C1 and C2 of the invention may be provided in the form of foam which is applied to the hair. Foam formation is typically achieved by the use of a foaming agent incorporated within the composition in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides; polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

Further Aspects

The present invention further relates to a method for treating hair comprising carrying out the following sequence of steps:
  applying one or more polymeric sublayer(s) to the hair, and
  applying a composition A comprising at least one pigment as defined hereinbefore to the hair having a first (initial) colour to impart the hair with a second colour different to the first (initial) colour, wherein the at least one pigment has a $D_{50}$ particle diameter of 20 nm to 1 µm.

The present invention further relates to a method for treating hair comprising
  applying a composition A comprising at least one pigment as defined herein before to a first portion of the hair having a first initial colour to impart the first portion of the hair with a second colour different to the first initial colour, the at least one pigment having a $D_{50}$ particle diameter of 20 nm to 1 µm, the at least one pigment having a core-shell structure, wherein the core comprises an inorganic and/or organic material, and wherein the shell comprises at least one cationic polymeric shell layer.

The present invention also relates to a method for treating hair comprising carrying out the following sequence of steps:
  determining a target colour, wherein the target colour differs from a first initial colour of the hair,
  applying a composition A comprising at least one pigment to a first portion of the hair to impart the first portion of the hair with a second colour different to the first initial colour, and
  applying one or more hair colouring composition(s) C to a second portion of the hair to impart the second portion of the hair with a third colour different to the second colour, wherein the first and second portions have at least one first common area, and wherein at least one of i) and ii) is fulfilled:
    i) the third colour differs from the colour of the composition(s) C in at most 5%, particularly at most 2%, more particularly at most 1% of at least one of:
      a* value,
      b* value, and
      L* value, according to the CIE L* a* b* system;
    ii) the third colour differs from the predetermined target colour in at most 5%, particularly at most 2%, more particularly at most 1% of at least one of
      a* value,
      b* value, and
      L* value, according to the CIE L* a* b* system.

The present invention also relates to a kit for treating hair comprising:
  a first component comprising a composition A comprising a pigment as defined herein, and optionally
  a second component comprising a composition B1 comprising a cationic polymer as defined herein.

The present invention also relates to the use of a component comprising the composition A as defined hereinbefore for changing a hair colour from a first initial colour via a second intermediate colour to a third final colour, wherein the third final colour differs from a predetermined target colour in at most 5%, particularly at most 2%, more particularly at most 1% of at least one of:
  a* value,
  b*value, and
  L* value, according to the CIE L* a* b* system.

EXAMPLES

The following are non-limiting examples of the method of the present invention. The examples are given solely for the purpose of illustration and are not to be construed as limitations of the present invention, as many variations thereof are possible without departing from the spirit and scope of the invention, which would be recognized by one of ordinary skill in the art.

Hair Treatment with "White Pigment" and "LbL (Layer-by-Layer)"

In general, hair swatches were treated with "LbL Solution" and "White Pigment" to create a bright (whitish) surface on the hair. The hair swatches were provided from Kerling International Haarfabrik GmbH, Backnang, Germany. The "White Pigment" was provided from Merck KGaA, Darmstadt, Germany. The "White Pigment" had the following L*a*b* values, measured by using a Minolta spectrometer as described hereinbefore: L*: 78.08; a*:1.24; b*: 3.88. The "White Pigment" had a $D_{50}$ particle diameter of 1 µm measured with a Malvern Mastersizer 2000 as described hereinbefore.

More specifically, three blond hair swatches were provided. One was treated with a composition containing 5% pigment by total weight of the composition. The second hair swatch was treated with a composition containing 10% pigment by total weight of the composition. The third hair swatch was treated with a composition containing 15% pigment by total weight of the composition. The same was carried out with 3 brown hair swatches.

Treatment Protocol for Each Hair Swatch

In a first step, a composition containing 5% Polyethylenemine, Pigment in the respective concentration and water (in the respective concentration to arrive at 100%) was prepared. This composition was smoothly mixed with a brush and applied on the hair swatch. The total amount was 1 g per hair swatch. After the hair swatch was fully covered with the Polymer/Pigment composition the hair swatch was covered with a foil to protect it against drying out. The foiled hair swatch was put in an oven (~45° C. for a residence time of 15 min). Afterwards the hair swatch was rinsed with tap water. The rinsed hair swatch was dried smoothly with a towel and 0.5% solution of Dextransulfate in water was applied on top of the hair swatch. The hair swatch was again covered with foil and put in an oven (~45° C. for a residence time of 15 min). Afterwards the hair swatch was rinsed with tap water and dried with the blow dryer. In a subsequent step the hair swatch was measured by the Minolta Device to generate L*a*b* values. An untreated hair swatch for each hair type (blond and brown hair swatch) was measured accordingly as reference.

Results
The measured L*a*b* values were as follows:

TABLE 1

| Blond | L*(D65) | a*(D65) | b*(D65) | ΔE2000 |
|---|---|---|---|---|
| Reference | 22.06 | 3.71 | 3.93 | — |
| Pigment 5% | 31.43 | 1.59 | 1.04 | 4.99 |
| Pigment 10% | 43.63 | 0.91 | 0.11 | 9.90 |
| Pigment 15% | 51.81 | 0.12 | −0.49 | 13.94 |

TABLE 2

| Brown | L*(D65) | a*(D65) | b*(D65) | ΔE2000 |
|---|---|---|---|---|
| Reference | 46.32 | 6.81 | 18.24 | — |
| Pigment 5% | 45.78 | 5.1 | 12.51 | 3.51 |
| Pigment 10% | 52.47 | 3.72 | 9.43 | 6.53 |
| Pigment 15% | 61.92 | 1.79 | 5.15 | 12.01 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A method for treating hair comprising:
    A) applying a composition A comprising at least one pigment to a first portion of the hair having a first initial colour to impart the first portion of the hair with a second colour different to the first initial colour, wherein the at least one pigment has a $D_{50}$ particle diameter of 20 nm to 1 µm, and wherein the difference between the L* value of the second colour and the L* value of the first initial colour $L^*_{second\ colour} - L^*_{initial\ first\ colour}$ is ≥1, according to the International Commission on Illumination color space ("CIE L* a* b*") system; and
    B) prior to step A), providing in at least a second portion of the hair one or more polymeric sublayers, wherein the first and second portions of the hair have at least one first common area, wherein step B) comprises:
        B1) applying a composition B1 comprising one or more cationic polymers to the second portion of the hair.

2. The method according to claim 1, wherein the second colour has a L* $value_{L^*second\ colour}$ of ≥22, according to the CIE L* a* h* system.

3. The method according to claim 1, wherein the overall colour change, represented by ΔE where $ΔE=[(ΔL^*)^2+(Δa^*)^2+(Δb^*)^2]^{1/2}$, from the first initial colour to the second colour is ≥5.

4. The method according to claim 1 wherein the at least one pigment has a L* $value_{L^*Pigment}$ of ≥60 according to the CIE L* a* b* system, and optionally, wherein the at least one pigment has a surface zeta potential of ≥±15 mV.

5. The method according to claim 1 wherein the at least one pigment has a core-shell structure, wherein the core comprises an inorganic and/or organic material, and wherein the shell comprises at least one cationic polymeric shell layer different to the material of the core.

6. The method according to claim 5, wherein the core comprises an inorganic material selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminium sulfosilicates, CI 77007, Pigment Blue 29), chromium oxide hydrate (CI 77289), Prussian blue (ferric ferrocyanide, CI 77510), carmine (cochineal), zinc sulfide, barium sulfate, zinc oxide, siliconised titanium dioxide, siliconised zinc sulfide, siliconised zinc oxide, and mixtures thereof.

7. The method according to claim 1, wherein step B) further comprises
    B2) applying a composition B2 comprising one or more anionic polymer(s) to the second portion of the hair after step B 1).

8. The method according to claim 7, wherein the cationic polymer(s) are selected from the group consisting of polyethyleneimine, polyallylamine hydrochloride, polyvinylarnine, copolymers thereof and mixtures thereof.

9. The method according to claim 7, wherein the anionic polymer(s) are selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and mixtures thereof.

10. The method according to claim 1, further comprising, after step A):
    C) colouring the hair by applying hair colouring composition(s) to at least a third portion of the hair, wherein the first and third portions of the hair have at least one second common area, wherein optionally, the hair colouring composition(s) comprise coloured polymer(s).

11. The method according to claim 10, wherein step C) comprises C1) applying a composition C1 comprising one or more cationic polymer(s), to the third portion of the hair, wherein optionally the cationic polymer(s) are cationic coloured polymer(s), and/or
    C2) applying a composition C2 comprising one or more anionic polymer(s) to the third portion of the hair after step C1), wherein optionally, the anionic polymer(s) are anionic coloured polymer(s).

12. The method according to claim 11, wherein the cationic coloured polymer(s) and/or the anionic coloured polymer(s) comprise at least one chromophore and/or at least one fluorophore, wherein the chromophore(s) are selected from the group consisting of nitrobenzene, azo, imine, hydrazine, phenothiazine, xanthene, phenanthridine, phthalocyanin and triarylmethane-based dyes, derivatives thereof, derivatives obtained from direct dyes containing a carbonyl group, acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyri done, pyrazoloquinazolone, perinone, quinacridone, quinophthalone, indigoid, thioindigo, naphthalimide, anthrapyrimidine, diketopyrrolopyrrole and coumarin dyes, derivatives thereof and mixtures thereof, and the fluorophore(s) are selected from the group consisting of derivatives from di-, tetra- or hexa-sulfonated triazine-stilbenes, coumarins, imidazolines, diazoles, triazoles, benzoxazolines, biphenyl-stilbenes optical brighteners, and mixtures thereof.

13. The method of claim 1 wherein the at least one pigment has a core-shell structure comprising:
    a core comprising an inorganic and/or organic material, and a shell comprising at least one cationic polymeric shell layer different to the material of the core, the shell at least partially encompassing the core.

14. A kit for treating hair comprising:
a first component comprising a composition A comprising a pigment as defined in claim 1, wherein application of the pigment to a portion of hair having a first initial colour imparts a second colour different from the first color, and wherein the difference between the L* value of the second colour and the L* value of the first initial colour $L^*_{second\ colour} - L^*_{initial\ first\ colour}$ is $\geq 1$, according to the CIE L* a* b* system:
a second component comprising a composition B1 including one or more cationic polymers; and
a third component comprising a coloring composition C.

15. The kit of claim 14, wherein the second component further comprises a composition B2 including one or more anionic polymers.

16. A method for treating hair comprising:
A) applying a composition A comprising at least one pigment to a first portion of the hair having a first initial colour to impart the first portion of the hair with a second colour different to the first initial colour, wherein the difference between the L* value of the second colour and the L* value of the first initial colour $L^*_{second\ colour} - L^*_{initial\ first\ colour}$ is $\geq 1$, according to the CIELAB color space ("CIE L* a* b*") system; and
B) prior to step A), providing in at least a second portion of the hair one or more polymeric sublayers, wherein the first and second portions of the hair have at least one first common area, and applying at least one composition B1 comprising one or more cationic polymers to the second portion of the hair; and
C) colouring the hair by applying at least one hair colouring composition to at least a third portion of the hair, wherein the first and third portions of the hair have at least one second common area, and wherein at least one the hair colouring composition comprises one or more coloured polymers.

17. The method according to claim 16, wherein step B) further comprises:
B2) applying a composition B2 comprising one or more anionic polymers to the second portion of the hair after step B1).

18. The method according to claim 16, wherein step C) comprises:
C1) applying a composition C1 comprising one or more cationic polymers to the third portion of the hair; and
C2) applying a composition C2 comprising one or more anionic polymer(s) to the third portion of the hair after step C1),
wherein at least one of the one or more cationic polymers and the one or more anionic polymers comprises a coloured polymer.

19. The method according to claim 18, wherein the at least one pigment has a $D_{50}$ particle diameter of 20 nm to 1 μm.

* * * * *